United States Patent
Lande

(10) Patent No.: US 7,699,814 B2
(45) Date of Patent: Apr. 20, 2010

(54) SYRINGE SHEATH

(75) Inventor: Lloyd J. Lande, Sumner, IA (US)

(73) Assignees: Ralph Lande, Sumner, IA (US); Beverly Lande, Sumner, IA (US)

( * ) Notice: Subject to any disclaimer, the term of this patent is extended or adjusted under 35 U.S.C. 154(b) by 945 days.

(21) Appl. No.: 11/131,657

(22) Filed: May 17, 2005

(65) Prior Publication Data

US 2006/0264887 A1 Nov. 23, 2006

(51) Int. Cl.
*A61M 5/32* (2006.01)
(52) U.S. Cl. .................. 604/198; 604/192; 604/197
(58) Field of Classification Search ............. 604/110, 604/187, 192, 194, 195, 197–199, 263, 188, 604/264, 268, 272, 535; 128/919; 600/5; 588/16; 250/505.1, 506.1, 515.1
See application file for complete search history.

(56) References Cited

U.S. PATENT DOCUMENTS

| | | | |
|---|---|---|---|
| 4,631,057 A | 12/1986 | Mitchell et al. | |
| 5,116,326 A | 5/1992 | Schmidt | |
| 5,120,309 A | 6/1992 | Watts | |
| 5,370,628 A | 12/1994 | Allison et al. | |
| 5,624,400 A | 4/1997 | Firth et al. | |
| 5,746,215 A | 5/1998 | Manjarrez | |
| 5,971,953 A * | 10/1999 | Bachynsky | 604/90 |
| RE37,439 E | 11/2001 | Firth et al. | |
| 6,589,209 B1* | 7/2003 | Dysarz | 604/110 |
| 6,712,793 B1 | 3/2004 | Geiger et al. | |
| 6,776,775 B1 | 8/2004 | Mohammad | |
| 2003/0093035 A1 | 5/2003 | Mohammed | |
| 2003/0163092 A1* | 8/2003 | Parker et al. | 604/198 |

FOREIGN PATENT DOCUMENTS

| | | |
|---|---|---|
| FR | 2 806 917 A1 | 10/2001 |
| FR | 2 821 562 A1 | 9/2002 |
| WO | WO 00/56383 A1 * | 9/2000 |
| WO | 01/74428 A1 | 10/2001 |

* cited by examiner

*Primary Examiner*—Nicholas D Lucchesi
*Assistant Examiner*—Nathan R Price
(74) *Attorney, Agent, or Firm*—McKee, Voorhees & Sease, P.L.C.

(57) ABSTRACT

A syringe assembly has a safety sheath to prevent accidental pricking of the user after injecting fluid from the syringe into an injection site of a patient. The syringe assembly includes a body, a needle, and a slidable plunger. A tube is slidably mounted on the rear end of the plunger and has a thumb tab for pushing the plunger forwardly in the syringe body. The syringe body extends through a protective sheath. After the fluid is injected from the syringe body into the patient, the user pulls rearwardly on the finger flange so as to force the plunger into the tube and thereby pull the needle into the sheath, as the needle is being withdrawn from the patient. The needle is automatically enclosed by the sheath using only one hand and without gripping the sheath.

11 Claims, 1 Drawing Sheet

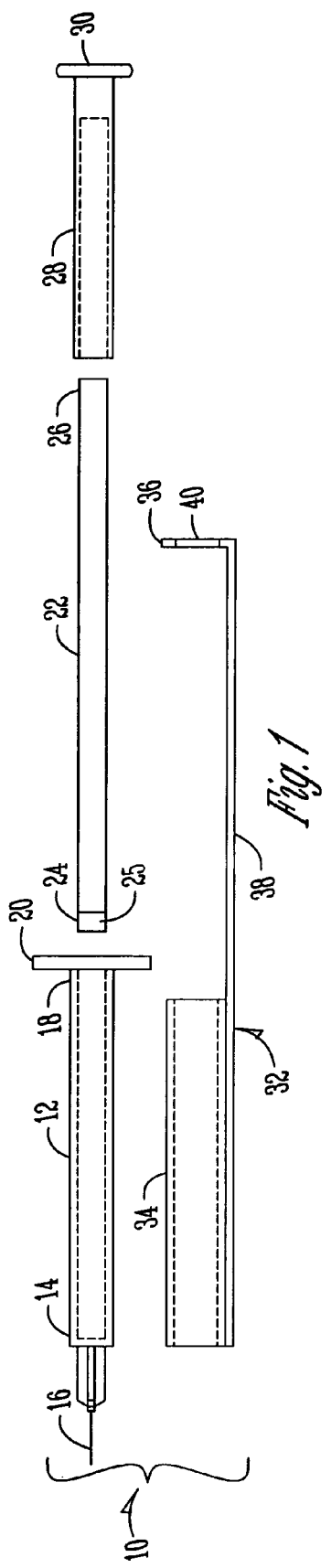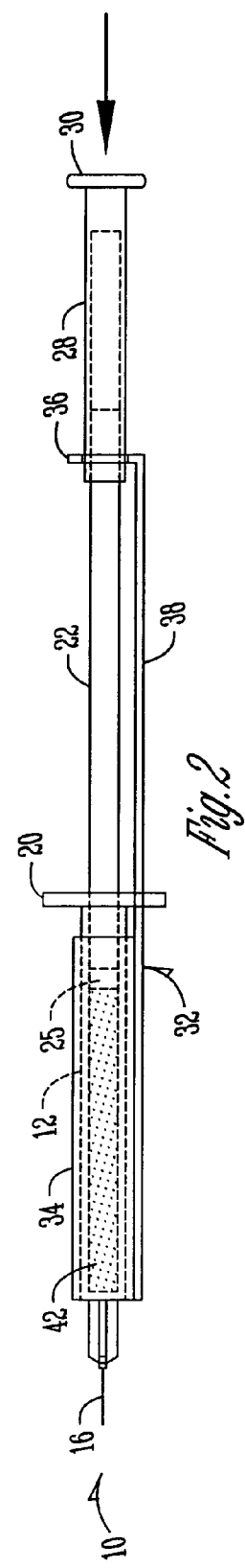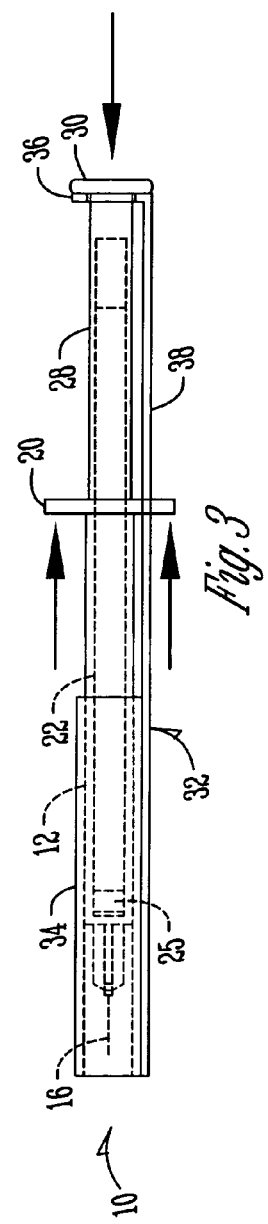

SYRINGE SHEATH

BACKGROUND OF THE INVENTION

Nurses, medical technicians, and medical assistants are repeatedly subjected to accidental needle pricks when using a syringe on a patient. Such accidents often happen after the injection when the user is holding the syringe in one hand and trying to place a cover over the needle with the other hand. Invariably, if a user is not focused or becomes distracted, accidental pricks will occur, thus exposing the user to the risk of contracting communicable diseases.

Therefore, a primary objective of the present invention is the provision of a syringe sheath which protects the user from accidental pricks.

Another objective of the present invention is the provision of a syringe sheath which is easy to use.

A further objective of the present invention is the provision of a syringe sheath which can be operated using only one hand.

Still another objective of the present invention is the provision of a syringe sheath which does not require gripping of the sheath by the user.

Yet another objective of the present invention is the provision of a syringe sheath which automatically covers the needle as the needle is withdrawn from the patient's injection site.

A further objective of the present invention is the provision of a method of safely using a syringe.

Another objective of the present invention is the provision of a syringe sheath which is economical to manufacture.

These and other objectives will become apparent from the following description of the invention.

BRIEF SUMMARY OF THE INVENTION

The syringe sheath of the present invention is adapted for use with a modified syringe assembly. The syringe assembly includes a body with a needle extending from the front end and a plunger slidably mounted in the rear end of the body. The plunger is modified by adding a tube slidably mounted on the plunger, with an enlarged thumb head on the rear end of the tube. The protective sheath has a first end with a tubular member through which the syringe body slidably resides and a second end through which the tube on the plunger slidably resides. The needle is moveable from a first position outside the sheath for injecting a fluid into the injection site of a patient, and a second position within the sheath after the injection is completed so as to prevent accidental sticking of anyone with the needle. The sliding connection between the plunger and the tube allows the plunger to be retracted into the tube after injection is completed, so that the needle automatically moves into the sheath as the needle is withdrawn from the injection site.

In the inventive method for safely using the syringe, the body of the syringe assembly is extended through the tubular sheath so that the needle extends beyond the sheath. The needle can then be inserted into a vial to draw fluid from the vial into the syringe body by partially withdrawing the plunger rearwardly from the body. The needle is then stuck into the injection site of a patient. The syringe user places his/her fingers in front of the finger tabs on the syringe body and pushes on the thumb head of the tube with his/her thumb to push the plunger forwardly into the syringe body until all of the fluid is injected into the injection site. Then, the user pulls rearwardly on the finger tabs while maintaining thumb contact with the thumb head, so as to slide the plunger into the tube and pull the needle rearwardly into the sheath so that the user is protected from accidental sticking by the needle. This safety method automatically pulls the needle into the sheath as the needle is withdrawn from the injection site. This safe method of using a syringe is accomplished without gripping the sheath and with only one hand of the user.

BRIEF DESCRIPTION OF THE DRAWINGS

FIG. 1 is an exploded view of the syringe components and the safety sheath of the present invention.

FIG. 2 is a view of the assembled syringe and sheath with the syringe filled with fluid and ready to be injected into a patient.

FIG. 3 is a view of the assembled syringe and sheath after injection of the fluid into the patient is completed, with the needle withdrawn into the sheath.

DETAILED DESCRIPTION OF THE PREFERRED EMBODIMENT

A syringe assembly 10 includes a conventional body 12 having a first or forward end 14 with a needle 16 extending therefrom, and a second or rearward end 18 having a finger flange 20 thereon. The finger flange 20 has opposing tabs extending from opposite sides of the body 12.

The syringe assembly 10 includes a plunger 22 having a first or forward end 24 adapted to be slidably received within the syringe body 12, and a second or rearward end 26 slidably received within a tube 28. The forward end 24 of the plunger 22 includes a conventional sealing element, such as a rubber stopper 25, to preclude leakage of fluid from the syringe body 12. The rearward end of the tube 28 includes an enlarged thumb tab 30.

The syringe assembly 10 also includes a sheath 32 having a first or forward end with a tubular member 34 and a second or rearward end with a flange 36. A connecting element 38 extends between the tubular member 34 and the flange 36 of the sheath 32. The tubular member 34 of the sheath 32 is adapted to slidably receive the syringe body 12 of the syringe assembly 10. The flange 36 of the sheath 32 includes a hole 40 through which the plunger tube 28 slidably extends.

In the initial setup of the syringe assembly, the rearward end 26 of the plunger 22 is received a short distance into the tube 28, as shown in FIG. 2. The syringe body 12 is extended through the tubular member 34 of the sheath 32 such that the needle 16 extends forwardly therefrom. The forward end 24 of the plunger 22 is received in the syringe body 12. The assembled syringe 10 can then be filled with a fluid 42 to be injected into a site in a patient. The filling of the syringe body 12 with the fluid 42 is done in a conventional manner, with the needle 16 inserted into a vial, and then withdrawing the plunger 22 from the forward end 14 of the body 12 until a desired volume of fluid 42 is drawn into the syringe body 12. The needle 16 is then removed from the vial and the plunger 22 moved slightly forwardly to assure that air bubbles are ejected from the syringe body 12, in a conventional manner.

The needle 16 is then stuck into the injection site of the patient. The user then places his/her fingers in front of the finger flange 20 with his/her thumb on top of the thumb tab 30, also in a conventional manner. The user then pushes on the thumb tab 30 to advance the plunger 22 to the forward end of the syringe body 12 so as to inject all of the fluid in the syringe body 12 into the injection site. Then, the user pulls rearwardly on the finger flange tabs 20 while maintaining pressure on the thumb tab 30, thereby forcing the plunger 22 rearwardly into the tube 28 and accordingly pulling the needle 16 into the tubular member 34 of the sheath 32, as shown in FIG. 3. Thus, the needle 16 is automatically moved into the sheath 32 as the needle 16 is withdrawn from the patient. Such covering of the needle 16 by the sheath 32 is accomplished using only one hand, and without the user gripping the sheath 32. The flange 36 on the sheath 32 engages the thumb tab 30, as seen in FIG. 3, to preclude the sheath from moving rearwardly relative to the syringe body 12, such that the needle 16 does not become accidentally exposed. After use, the syringe 10 can be disposed in a conventional safe manner.

The plunger 22 and tube 28 have a friction fit sufficient to preclude relative movement between the plunger 22 and the tube 28 as the fluid is being ejected from the body 12, and then allowing the plunger 22 to be forced into the tube 28 after the forward end 24 of the plunger 22 engages the forward end 14 of the body 12.

It is understood that the user may be a doctor, nurse, or medical technician or assistant. The user may also be the patient himself/herself, such as a diabetic person giving himself/herself an insulin shot. It is further understood that the user could be a veterinarian or others using the syringe to inject animals.

The invention has been shown and described above with the preferred embodiments, and it is understood that many modifications, substitutions, and additions may be made which are within the intended spirit and scope of the invention. From the foregoing, it can be seen that the present invention accomplishes at least all of its stated objectives.

What is claimed is:

1. A syringe assembly, comprising:
    a syringe body with opposite front and rear ends, the body being adapted to hold fluid to be injected into a patient;
    a needle extending from the front end of the syringe body;
    a plunger slidably mounted in the rear end of the syringe body;
    a tube slidably mounted on the plunger and having an enlarged thumb tab; and
    the plunger and tube having smooth mating cylindrical surfaces for sliding movement of the plunger into the tube;
    a protective sheath having a longitudinal axis, and a tubular forward end in which the syringe body slidably resides and a rear end with a flange extending from the sheath toward the tube and perpendicular to the longitudinal axis, the flange having an opening through which the tube slidably resides such that the sheath is mounted to both the syringe body and to the tube;
    wherein the needle is movable from a first position outside the sheath for injecting the fluid into a patient and a second position within the sheath to prevent accidental sticking by the needle.

2. The syringe assembly of claim 1 wherein the plunger moves from an extended position to a retracted position in the tube as the needle moves into the sheath.

3. The syringe assembly of claim 1 wherein when the plunger reaches the forward end of the syringe body, the syringe body is pulled rearwardly to retract the plunger into the tube and thereby retract the needle into the sheath.

4. The syringe assembly of claim 1 wherein the flange engages the thumb tab and thereby preclude rearward movement of the sheath after the needle is moved into the sheath.

5. The syringe assembly of claim 4 wherein the flange has a hole through which the tube slidably extends.

6. The syringe assembly of claim 5 wherein the sheath includes a connecting element extending between the tubular member and the flange and along one side only of the plunger.

7. The syringe assembly of claim 1 wherein the needle is withdrawn into the sheath using only one hand.

8. The syringe assembly of claim 1 wherein the needle is withdrawn into the sheath without gripping the sheath.

9. The syringe assembly of claim 1 wherein the plunger and tube have fixed diameters.

10. The syringe assembly of claim 1 wherein the mating surfaces of the plunger and tube frictionally engage throughout the sliding movement.

11. The syringe assembly of claim 1 wherein the syringe body and the tube do not overlap.

* * * * *